United States Patent [19]

Raab

[11] 4,336,618
[45] Jun. 29, 1982

[54] BONE CONNECTIVE PROSTHESES ADAPTED TO MAXIMIZE STRENGTH AND DURABILITY OF PROSTHESES-BONE CEMENT INTERFACE; AND METHODS OF FORMING SAME

[76] Inventor: Simon Raab, 5872 Westbury Ave., Montreal, Quebec H3W 2W9, Canada

[21] Appl. No.: 221,574

[22] Filed: Dec. 31, 1980

Related U.S. Application Data

[62] Division of Ser. No. 45,657, Jun. 5, 1979, Pat. No. 4,281,420.

[30] Foreign Application Priority Data

Feb. 15, 1979 [GB] United Kingdom ............... 7905445

[51] Int. Cl.³ ............................................. A61F 1/04
[52] U.S. Cl. ........................................ 3/1.913; 3/19; 128/92 CA
[58] Field of Search ............... 134/1, 41; 128/92 C, 128/92 CA; 3/1.9, 1.91, 1.911, 1.912, 1.913; 156/232; 428/463, 520; 427/2, 388.2, 388.5, 327

[56] References Cited

U.S. PATENT DOCUMENTS

| | | | |
|---|---|---|---|
| 3,078,180 | 2/1963 | Zander et al. | 134/41 |
| 3,647,498 | 3/1972 | Dougherty | 427/2 |
| 3,649,345 | 3/1972 | Tolosa | 427/2 |
| 3,713,860 | 1/1973 | Auskern | 128/92 C |
| 3,790,507 | 2/1974 | Hodosh | 3/1.9 |
| 3,907,609 | 9/1975 | Coggins | 134/41 |
| 3,938,198 | 2/1976 | Kahn et al. | 3/1.913 |
| 4,065,817 | 1/1978 | Branemark et al. | 3/1.91 |
| 4,202,055 | 5/1980 | Reiner et al. | 3/1.91 |

OTHER PUBLICATIONS

Ingwersen, O. S. et al., Editors, *The Knee Joint*, American Elsevier Publishing Co., Inc., New York, 1974, pp. 1-5.

Hench, L. L., "Ceramic Implants", University of Florida, Gainsville, Fl., 1975.

*Primary Examiner*—Richard L. Chiesa
*Assistant Examiner*—Chris Konkol
*Attorney, Agent, or Firm*—Roylance, Abrams, Berdo & Farley

[57] ABSTRACT

There is disclosed a prosthesis comprising a prosthetic element and a polymethylmethacrylate film fixedly adhered thereto. The prosthesis comprises a surface adapted to be fixedly attached to bone and bears a polymethylmethacrylate film upon the attachment surface. The polymethylmethacrylate film is adhered to the prosthetic element by a process which comprises treating the prosthetic element surface to eliminate any weak boundary layer, applying polymethylmethacrylate to the treated surface, and thereafter annealing the polymethylmethacrylate film.

56 Claims, 5 Drawing Figures

BONE CONNECTIVE PROSTHESES ADAPTED TO MAXIMIZE STRENGTH AND DURABILITY OF PROSTHESES-BONE CEMENT INTERFACE; AND METHODS OF FORMING SAME

This is a division of application Ser. No. 45,657, now U.S. Pat. No. 4,281,420, filed June 5, 1979.

BACKGROUND OF THE INVENTION

1. Field of the Invention

The present invention relates to prostheses adapted to be fixedly attached to bone by means of a bone cement. Specifically, the present invention is directed towards prostheses adapted to maximize the strength and durability of the prostheses/bone cement adherence.

2. Description of the Prior Art

In the field of orthopedic surgery, ZIMALOY manufactured by Zimmer, U.S.A., Inc., a chromiun-cobalt-molybdenum alloy, stainless steel, titanium alloys, and polymerized materials such as ultra high molecular weight polyethylene (hereinafter UHMWPE) have been used successfully to replace the ends of long bones and joints, including the hip joint. However, there exists a severe limitation with respect to such orthopedic surgery, namely, coupling of the prostheses to bone. Due to such factors as mechanical stress, fatigue, corrosion, etc., the prostheses/bone cement joints have been prone to failure.

Present methods of utilizing such bone prostheses involve the use of a prosthesis having a stem portion which is inserted into the interior of a bone. A bone cement comprising a mixture of polymethylmethacrylate (hereinafter PMMA) polymer and methyl methacrylate monomer and optionally including a styrene copolymer of PMMA is likewise inserted into the bone cavity and is utilized to couple the stem of the implant to the bone itself. Experience has demonstrated, however, that serious drawbacks exist with respect to the coupling between the prosthesis stem and the bone cement. Attempted solutions to this problem have been directed primarily toward strengthening the prosthesis/bone cement interface by means of gross mechanical interlock involving, for example, dove tails, small stems, etc. Such devices result in stress concentrations that can exceed the strength of the bone cement as well as cause non-physiological force distribution in the bone.

Adherence at the interface between the implant and PMMA is greatly restricted by current industrial and surgical practices. For instance, the PMMA cement is typically applied in a highly viscous doughy state with the result that the degree of contact between the implant and the cement is inadequate. Moreover, the existence of weak boundary layers such as contaminants and weak metal oxides on the surface of the implant have also caused problems. Weak boundary layers may be due to the composition of the implant or to the process of forming the same. Thus, in the case of a metal implant, the surface of the implant normally includes weak metal oxides as weak boundary layers. In the case of a polymeric implant, the surface of the implant normally includes a weak boundary layer comprising monomer, partially polymerized or low molecular weight polymer and contaminants comprising mold release agents, etc. Finally, the implant may come in contact with air, blood, water, etc. prior to being inserted into the bone thereby becoming contaminated. The existence of weak boundary layers, e.g., surface contaminants, is detrimental to the formation of good implant-bone cement adherence. Thus, the strength of such joints has been dependent upon gross mechanical interlock. Such difficulties in the formation of a satisfactory prosthesis/bone cement connection have also caused the result that mere resurfacing of a deteriorated joint, e.g., a deteriorated hip joint due to arthritis, was not readily accomplished. Thus, in the case of a deteriorated articular surface, e.g., surface of the head or ball in a ball and socket joint, the entire head of the bone is generally removed and a prosthetic head connected to the bone by means of a stem inserted into the interior of the bone, although in some instances, resurfacing implants have been used with bone cement.

SUMMARY OF THE INVENTION

It has now been discovered that prosthesis fixation problems may be overcome by treating at least that portion of the prosthesis which is adapted to be connected to bone in order to provide a PMMA film fixedly adhered to said portions of the prosthesis. Prior to the application of the PMMA film, the surface to be coated is treated to eliminate any weak boundary layer existing thereon. Therafter, a PMMA film is applied by dipping, painting, spraying, etc., and finally, after the film has dried, it is annealed to remove any stresses in the film.

The resultant prosthesis has a film of PMMA firmly adhered to the surface thereof. This PMMA film adhesively interacts molecularly with PMMA bone cement. Accordingly, the adherence of a prosthesis adhesively connected to bone by means of a PMMA cement can be drastically increased.

BRIEF DESCRIPTION OF THE DRAWINGS

In the drawings which form a part of the original disclosure of the present invention.

DETAILED DESCRIPTION OF THE INVENTION

According to the present invention, prostheses exhibiting marked fixation improvements have been discovered. Such a prosthesis comprises a prosthetic element having a PMMA film fixedly adhered to at least a portion of the surface of the prosthetic element. The prosthesis includes a surface adapted to be fixedly attached to bone or a bone attachment surface. At least the bone attachment portion of the surface, in accordance with the present invention, is coated with a PMMA film prior to attachment to bone. The PMMA coating or film is adhered to the prosthetic element by a process which comprises treating the element surface to eliminate any weak boundary layer which may be present; applying PMMA to the treated surface; and annealing the PMMA film.

Figure 1:
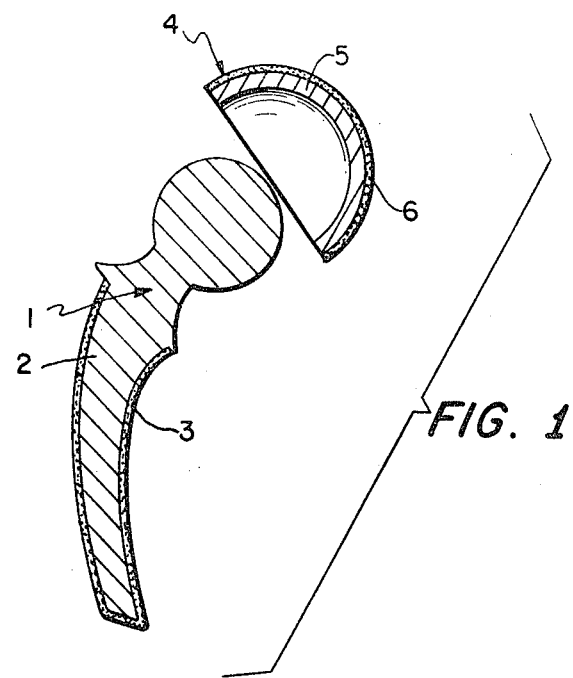
FIG. 1 is an elevational side view in longitudinal section of a PMMA coated hip prosthesis prepared in accordance with the present invention.

FIG. 1 is an elevational side view in longitudinal section of a stem insertion hip joint prosthesis having a bone attachment surface bearing a PMMA film. Also shown is a resurfacing prostheses for the socket portion of a hip joint, with the bone attachment surface having a PMMA film fixedly adhered thereto in accordance with the present invention. Thus, in FIG. 1 there is shown a stem insertion prosthesis 1, comprising a rigid prosthetic element 2, which may be composed of a metal alloy or a polymer such as UHMWPE, bearing a thin, high strength PMMA film 3. Also shown is a resurfacing prosthesis 4 for the socket portion of a ball and socket joint, comprising a rigid prosthetic element 5 and a PMMA film 6.

The rigid prosthetic element which is coated in accordance with the present invention may be chosen from any suitable material including metal alloys and plastic. Thus, the element may be composed of a titanium alloy, stainless steel, a cobalt-chromium or cobalt-chromium-molybdenum alloy, MP-35 (protozol) or a polymeric material such as ultrahigh molecular weight polyethylene (UHMWPE).

In order to provide a high strength PMMA film in accordance with the present invention, the prosthetic element must first be prepared. Preparation involves removal of any contaminants which may act as weak boundary layers so that the coating may be joined directly to the prosthetic element with no intervening material. In the case of a metal prosthetic element, the weak boundary layer may comprise contaminants such as dirts and oils and additionally typically includes weak metal oxides. In the case of a polymeric prosthetic element, the weak boundary layer typically comprises contaminants such as unreacted monomer, anti-oxidation agents and mold release agents and additionally low molecular weight polymer.

In the case of a metal prosthetic element, removal of the weak boundary layer may involve a degreasing step. Removal of the weak metal oxides is accomplished by an acid treating step which may be followed by a desmutting and passivation step. However, any treatment which functions effectively to remove contaminants and weak metal oxides may be utilized.

The degreasing treatment may be carried out through the utilization of an aqueous alkaline solution, such as, for example, an aqueous solution of sodium hydroxide. Thus, the prosthetic element to be degreased may be immersed in a 1 N solution of sodium hydroxide which has been heated to its boiling point, for 30 minutes to remove contaminants and grease. Another degreasing treatment which may be utilized with less contaminated elements comprises exposing the prosthetic element to trichloroethylene vapor. In order to determine whether or not degreasing is complete, the "water break test" may be utilized according to which the degreased prosthetic element is rinsed in distilled water. When the element is removed from the water, if the water beads up and runs off in less than 30 seconds, the surface is not clean enough. There should be no break in the film of water nor any tendency of the film to crawl or pucker.

Subsequent to the degreasing treatment, the metallic prosthetic element should preferably be treated with an acid etching treatment in order to remove weakly bound metal oxides. Such treatment may comprise immersing the element in a sulfuric acid/water admixture at an elevated temperature of, for example, 60° C. for a period of approximately $\frac{1}{2}$ hour. Other treatments which may be utilized include immersing the prosthetic element in a sulfuric acid/sodium dichromate aqueous solution or treatment with other acid solutions.

It is preferred that the acid etching treatment be discontinued prior to the accomplishment of any gross surface changes. Thus, it is preferred that the surface which is designed to be attached to bone, be smooth. This results in a more continuous stress concentration about the prosthetic element/bone cement interface. However, where it is desired to use an implant having a rough surface thus promoting a greater degree of mechanical interlock, the coating of the present invention may be utilized and a stronger joint will result.

In the case of an alloy prosthetic element which has been acid etched such as with the sulfuric acid solution discussed above, completion of the etching reaction will be evidenced by a reaction which turns the surface of the element black. This is due to the presence of carbon which is a component of metal alloys. Such presence of carbon indicates that the surface has been sufficiently etched. If no carbon appears, etching is not complete. In order to avoid any gross surface changes, the element should be removed from the etching solution within ten seconds of the appearance of carbon. The etched element may be checked by means of a Hobsyn Tally Surface Profile or an SEM to insure that no gross surface changes have occurred.

Thereafter, any carbon remaining on the surface of the element may be removed by means of a desmutting and passivation treatment. Such desmutting and passivation treatment may be carried out by means of a hydrofluoric acid/nitric acid aqueous admixture heated to an elevated temperature of approximately 60° C. Other strong oxidation reagents may be utilized if desired. When the etched element is immersed in such a solution, there should be a reaction within seconds evidenced by a burst of bubbles as carbon is removed. This is followed by another sudden burst of bubbles evidencing a secondary reaction. At this point, the element should be removed from the desmutting and passivation solution. This treatment functions not only to remove carbon but additionally promotes the formation of a well adhered, uniform, high strength oxide surface, and is a preferred treatment step.

The initial removal of weak boundary layers may be carried out not only by chemical means, i.e., degreasing and acid etching, but mechanical means may be utilized if desired. Thus, the prosthetic element may be treated by blasting with alumina grit to provide a virgin metal surface. Other mechanical treatments such as grinding, honing, machining, etc., may also be utilized.

Following mechanical treatment of the prosthetic element, the treated surface should immediately be immersed in a passivation solution comprising, e.g., nitric and hydrofluoric acid, as above. It is preferred that the passivation treatment be carried out within a short time from the mechanical treatment. The lapse of time between mechanical treatment and passivation should preferably be less than one minute.

Thereafter, the treated element should be rinsed in water until the water has a neutral pH. The treated element should thereafter be dried by any suitable means such as by heating in an oven or by blowing the surface dry with a warm air stream.

Once the element has dried, it is allowed to cool to room temperature prior to application of the PMMA film thereto. Care must be taken that the clean surface not be contaminated during drying or cooling. Coupling agents such as siloxane derivatives may be applied before the coating.

Thereafter, the PMMA film is applied to the prosthetic element. The film may be applied by means of painting, spraying, dipping, powder coating, electrostatic coating, or in any other suitable manner in the form of a lacquer, powder or emulsion. The method and form utilized will depend on a number of various factors including the desired coating thickness, strength, implant geometry and surface roughness.

The film consists essentially of PMMA. However, other materials may be included in the film such as cross-linking agents, free radical catalysts, activators, plasticizers, chain transfer agents, inhibitors, plasticizing co-polymers, as well as adhesion promoters in the form of co-polymers, such as of acrylic acid and other freely orienting polar molecules.

One preferred method of applying the film to the prosthetic element comprises the application of a PMMA lacquer to the element. Application may take the form of dipping, spraying, etc. A PMMA lacquer is prepared by dissolving PMMA high molecular weight beads in a solvent such as dichloromethane. A small amount of barium sulfate may be added to the lacquer in order to keep the coated surface from crazing as well as making the coating radio opaque. The concentration of polymer in the solution should be in the range of 0.01 g. per ml. to about 0.8 g. per ml., preferably from about 0.2 g. per ml. to about 0.4 g. per ml., most preferably from about 0.25 g. per ml. to about 0.35 g. per ml.

The element is immersed in the lacquer for a period of time sufficient to form a suitable coating on the surface of the element. Such period of time may range from about 5 seconds to about 60 minutes, preferably from about 15 minutes to about 60 minutes, most preferably from about 25 to 35 minutes.

Another method of applying the film to the prosthetic element comprises the application of PMMA dissolved in methylmethacrylate (MMA), and additionally containing a conventional curing catalyst. Still another method of applying the PMMA coating is to coat the prosthetic element with MMA and catalyst. In cases where MMA is used, a high temperature curing step follows the coating to polymerize the MMA to PMMA. This may constitute the annealing step discussed hereinafter.

Upon completion of the application of PMMA to the element, the PMMA film should be annealed by exposing the coated element to a temperature above that of the glass transition temperature of PMMA, i.e., 70°–90° C., preferably 80° C. The curing or annealing treatment is necessary to insure complete polymerization and removal of any volatile components from the film. High pressures, i.e. greater than 100 psi may be applied to inhibit bubble formation. Moreover, by heating the film to a temperature above the glass transition temperature of PMMA, any mechanical stresses in the film developed during the drying thereof will be eliminated.

The rate at which the coated element is cooled following the annealing treatment is preferably carefully controlled to insure that it does not exceed about 1.5° C. per minute until the coated element reaches a temperature of about 80° C. This insures that only minimal stresses are formed in the film during cooling. If desired, the film may be crosslinked by chemical and/or radiation techniques.

The thickness of the film thus produced is not of critical importance; however, the preferred minimum thickness of the film should be about 0.0001 inch, more preferably about 0.001 inch, most preferably about 0.002 inch.

Upon completion of the annealing or curing of the PMMA film, the coated prosthetic element is ready for use as a prosthesis. If the prosthesis is a bone implant prosthesis, the interior of the bone is removed and cleaned and a PMMA bone cement is applied to the interior of the bone. Thereafter, the implant portion of the prostheses, coated in accordance with the present invention is inserted into the interior of the bone. If desired, the coating may be softened with a solvent such as MMA monomer prior to insertion into the bone. This causes the PMMA film to swell and soften, thus allowing for greater mechanical and chemical interaction between the coating and bone cement.

Figure 2:
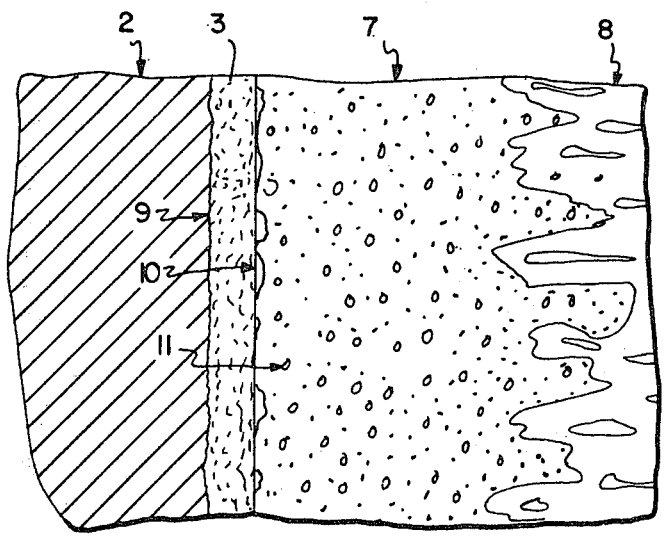
FIG. 2 illustrates an enlarged fragmentary view of a PMMA coated bone implant, as shown in FIG. 1, which has been fixedly adhered to the interior of a bone by means of a PMMA bone cement.

In FIG. 2, an enlarged fragmentary view of a coated prostheses which has been fixedly adhered to bone by means of a PMMA bone cement is illustrated. Prosthetic element 2 is connected to bone cement 7 via the PMMA film 3. Bone 8 is shown to be adhered to the bone cement. The interface 9 between the PMMA film and the element is shown to be free of defects and any weak boundary layer due to the precoating treatment of the element. The interface between the PMMA coating and bone cement 10, represents both a chemical and mechanical adherence. Flaws 11 in the bone cement 7 may be displaced away from the interface 9 due to the interaction of the film and cement.

Where a prosthetic element comprising a polymer, especially UHMWPE is to be utilized, a somewhat different weak boundary layer removal treatment is utilized. Such treatment comprises either an oxidation treatment or a treatment referred to by the acronym "casing" (crosslinking by activated species of inert gases). The oxidation treatment may be performed by corona discharge, flame treatment or an acid treatment, such as chromic acid, etc. The oxidation treatment accomplishes the removal of contaminants and low molecular weight polymers, i.e., polyethylene.

It is preferred that the polymeric element be degreased prior to the oxidation or casing treatment. Such degreasing treatment is usually readily accomplished by immersing the polymeric element in trichloroethylene liquid for several seconds.

As previously mentioned, in lieu of surface oxidation treatment, the polymeric element may be treated by "casing". This process consists of allowing electronically excited species of rare gasses to impinge upon the surface of the polymer. As these metastable and ionic gasses come in contact with polyethylene, for example, they cause abstraction of hydrogen atoms and formation of polymer radicals at and near the surface of the polymer. The radicals formed by this process interact to form crosslinks and unsaturated groups without appreciable scission of the polymer chain. The mechanical strength of the surface region is increased remarkably by the formation of a gel matrix. Thus, a weak boundary layer is transformed into a strong boundary layer. Wettability of the surface is relatively unaffected. Contact of the activated gas with the polymer surface for a time as short as one second will remarkably improve adhesive joint strength. Longer exposure times may be necessary when utilizing a more inert polymeric element such as, for instance, polytetrafluoroethylene. It is believed that substitution of casing for the oxidation treatment results in a more well adhered PMMA film.

Upon completion of the oxidation and/or casing treatment of the polymer surface, a PMMA coating is applied to the polymeric element in the same manner as previously discussed with respect to the metal element. The PMMA film should thereafter be annealed or cured as with the coated alloy element. Annealing at a temperature of about 100° C. is sufficient with a UHMWPE element.

When a PMMA coating is applied to a prosthetic element in accordance with the present invention, the resulting prosthesis may be joined to bone cement and will exhibit markedly superior adherence to the same when compared to the adherence of bone cement to an uncoated prosthesis or when compared to the adherence of a coated prosthesis wherein the element pre-coating treatment and/or where the annealing treatment is not utilized.

The effect of the improved adherence between the prosthesis and bone cement results not only in improved adhesion of bone implant prosthesis to the interior of a bone but moreover may eliminate in some cases the need for using an implant stem. Thus, stems have been used in prosthetics to implant a steel object securely into the bone. However, typically, the reason for the implant is a surface deterioration of the joint, for example, due to arthritis, but a mere resurfacing was not easily accomplished because of the fixation problems.

Figure 3:
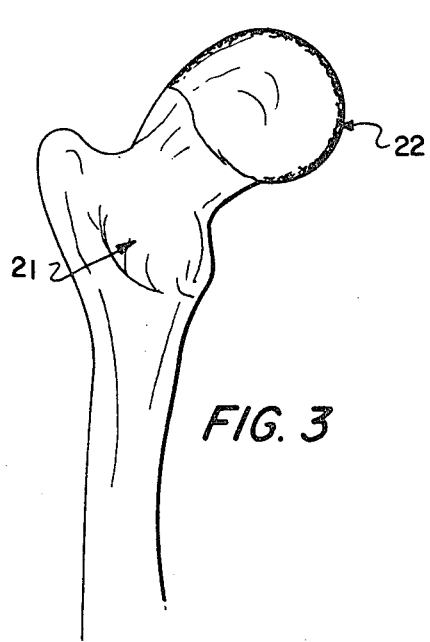
FIG. 3 is a side elevational view of a human femur having a deteriorated head surface.
Figure 4:
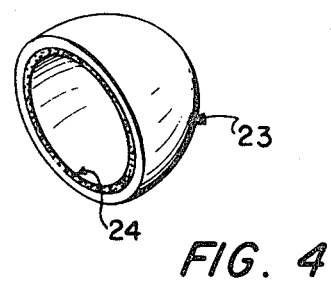
FIG. 4 is a perspective view of a prosthesis having a PMMA coating on the bone connective surface thereof. The prosthesis may be utilized for resurfacing a deteriorated head surface of a ball and socket joint thus obviating the need for the removal of the head portion of the joint.

Recent advances in the application of cement to bone involves the pressurization of cement deep into the pores of bones creating intimate interlock. The only problem remaining has been the attachment of a metal surface to the cement without a stem. Such problem may be solved utilizing the PMMA coated prostheses of the present invention. Thus, in FIG. 3 there is shown a human femur 21 in elevational side view, with the head thereof having a deteriorated surface 22, due to, for example, arthritis. In the past, it would have been preferred to remove the entire head of the femur and to substitute a prosthetic head connected to the femur by means of a stem insertion. However, by utilizing the present invention, an exterior surface may be fixedly attached to the deteriorated surface. The new prosthetic surface shown in FIG. 4 comprises a prosthetic element 23 which may be an alloy, and an inner surface 24 comprising PMMA. It can be strongly adhered to the head of the femur when prepared according to the process of the present invention, as shown in FIG. 5.

Figure 5:
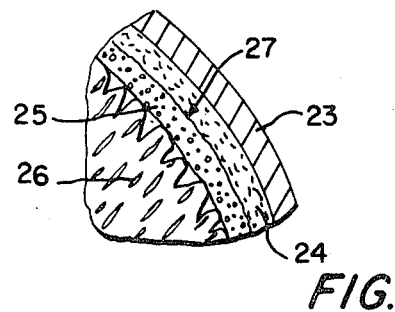
FIG. 5 illustrates an enlarged fragmentary cross-section of a deteriorated femur head bearing the resurfacing prosthesis of FIG. 4.

In FIG. 5 there is illustrated an enlargement of a fragmentary cross-section of a femur head after resurfacing. Bone cement 25 is shown extending deep into the surface of the bone 26. The bone cement is connected to the PMMA film 24; there being such forces as molecular bonding at the PMMA/PMMA-bone cement interface 27. The prosthetic element 23 is thus connected by means of the PMMA film and the bone cement to the resurfaced bone. Resurfacing prostheses of the present invention may be used not only for deteriorated ball and socket joints, but may be used in general on any deteriorated articular surface including, for example, a deteriorated knee.

The following examples serve to illustrate the formation of the prosthetic devices of the present invention and the improvement in results obtained by the use thereof.

EXAMPLE 1

Preparation of a PMMA Lacquer

Thirty grams of high molecular weight PMMA beads (manufactured by Fisher Chemical) are dissolved in 100 ml of dichloromethane with stirring. When all of the beads have dissolved, one gram of barium sulfate is added. The barium sulfate does not dissolve in the solution but rather, a portion becomes suspended in the solution rendering the solution opaque. The solution is allowed to stand for one-half hour in order to allow the barium sulfate to settle out. At the end of one-half hour the solution containing suspended barium sulfate is decanted from the barium sulfate sediment.

Preparation of a Cobalt-Chromium Stem Insert Prosthetic Element

The surface of a dry grit blasted cobalt-chromium alloy is to be coated. The element is first degreased by immersing it in 1 N solution of sodium hydroxide which has been heated to its boiling point. The alloy element is allowed to remain in the alkaline bath for 30 minutes. Thereafter, the element is removed from the bath and rinsed with warm water until the water tests neutral.

The thus treated element is thereafter acid etched by means of a 50% by volume aqueous sulfuric acid solution. The element is immersed in the solution at a temperature of 60° C. After about one-half hour a reaction which turns the surface black occurs. The element is removed from the acid solution and is rinsed in distilled water.

Following acid etching, the element is treated in a desmutting solution comprising an admixture of 15% by volume of a 52% hydrofluoric acid solution; 45% by volume nitric acid and 40% by volume water. The treated element is immersed in this solution at a temperature of from about 50 to about 60° C. After ten seconds, there is a burst of bubbles indicating the removal of carbon. This is followed by another sudden burst of bubbles indicating a secondary reaction. At this point the element is removed from the desmutting solution. Immediately upon removal the element is rinsed with distilled water until the water is neutral. The element is dried in an oven at a temperature of 110° C. for approximately 5 to 10 minutes. The element is removed from the oven and allowed to cool to room temperature.

Application of the Coating

The treated alloy element is immersed in the PMMA lacquer prepared earlier. After 30 minutes the element is removed from the lacquer and placed into an oven at 60° C. The element is left in the oven for two hours.

Annealing Procedure

The coated element is placed in an oven at 160° C. for 18 hours. The element is removed from the oven and allowed to cool at a rate of $1\frac{1}{2}$° C. per minute until the temperature is 70° C. Thereafter, the element is cooled in open air. It is important that the coated element not be cooled too quickly due to the differences in rate of thermal contraction between the coating and the substrate.

The PMMA film produced thereby has a thickness of between 0.001 and 0.0015 inch.

EXAMPLE 2

Preparation of a Polyethylene Element

A UHMWPE prosthetic element is to be coated. The element is passed over a butane-oxygen flame until all parts of the surface have been exposed to the flame. Thereafter, the treated element is exposed to activated species of an argon gas which have been generated by means of a high voltage discharge electrode in a vacuum chamber. The treated polyethylene element is thereafter allowed to cool to room temperature and is then coated with the PMMA lacquer as described in Example 1. The coated polyethylene element is dried in an oven at a temperature of 60° C. for two hours. Thereafter, the coating is annealed by heating the coated polyethylene element in an oven at 100° C. for two hours. The substrate is slowly allowed to cool as described in Example 1.

EXAMPLE 3

A stem insert sample is prepared and coated as described in Example 1. This sample and an uncoated stem insert sample are bonded to bone cement under ambient conditions. The interface shear strength as measured by a cylindrical lap shear strength test for each element measured in mega Pascals and pounds/sq. in. is determined to be as follows:

| Uncoated | | | Pretreated, Coated and Annealed | |
|---|---|---|---|---|
| MPa | (Standard Deviation) | psi | MPa | psi |
| 2.1 | (.5) | 305 | 15.2 (.7) | 2200 |

The cylindrical lap shear strength test (referred to above and in the following examples) is carried out as follows: A cylindrical sample to be tested is inserted into an annular mold containing PMMA/MMA bone cement and the cement is allowed to harden. The mold is removed to provide a cylindrical sample having an annular ring of bone cement bonded to a portion of the cylindrical surface. The sample is placed in a gripping device wherein it is gripped by means of the annular ring of bone cement. Force is applied axially to an end of the cylinder and the amount of force necessary to break the bond between the cylindrical sample and the annular ring of bone cement is recorded.

EXAMPLE 4

An alloy stem insert sample is prepared by degreasing it, coating it with PMMA and annealing it, all as described in Example 1. For purposes of comparison, another prosthetic element is prepared in the same way, except that instead of annealing treatment, the PMMA coating is cured at ambient temperature and is thereafter bonded to bone cement under ambient conditions. The interface shear strengths as measured by a cylindrical lap shear strength test for the two elements are determined to be as follows:

| Ambient Cured | | Annealed | |
|---|---|---|---|
| MPa | psi | MPa | psi |
| 3.9 (.9) | 479 | 6.2 (.7) | 900 |

EXAMPLE 5

PMMA coated stem insert samples are prepared as in Example 1. One is joined to bone cement under ambient conditions while another is exposed to intermedullary contents, wiped with a saline solution and thereafter joined to bone cement. The interface shear strengths of each are measured. There is no statistically significant difference in values.

The above tests are performed on uncoated stem inserts. The interface shear strength of the uncoated, uncontaminated sample is significantly less than the coated sample and moreover, the interface shear strength of the contaminated sample shows a 50% reduction in value with respect to the uncoated, uncontaminated sample.

Thus, it can be seen that prostheses prepared in accordance with the present invention are unaffected by contamination while untreated prior art prostheses are greatly influenced by contamination.

EXAMPLE 6

A UHMWPE sample is flame treated, coated with PMMA, dried and annealed as described in Example 2. This sample and an uncoated UHMWPE sample are bonded to bone cement under ambient conditions. The block shear strength for each sample is determined to be as follows:

| Uncoated | Coated | |
|---|---|---|
| MPa | MPa | psi |
| Less than .1 | 5.1 (.5) | 740 |

The "block shear strengths" referred to above are measured as follows. A cubical or block sample having a flat surface to be tested which is treated or untreated as desired, is provided. A cube or block of bone cement is formed on the surface to be tested, by means of, e.g., a mold. After hardening of the bone cement the sample is gripped by the cube of bone cement. Force is applied to the sample and the amount of force required to break the cement bond between the sample and the cube of bone cement is recorded.

What is claimed is:

1. A prosthesis comprising a prosthetic element and a polymethylmethacrylate film fixedly adhered to at least a portion of the surface of said prosthetic element;
   said prosthesis comprising a surface adapted to be fixedly attached to bone by means of bone cement;
   said prosthetic element bearing said polymethylmethacrylate film at least upon said attachment surface;
   said polymethylmethacrylate film being adhered to said prosthetic element by a process which comprises:
   treating said prosthetic element surface to eliminate any weak boundary layer;
   applying polymethylmethacrylate to said treated surface;
   and thereafter annealing said polymethylmethacrylate film.

2. A prosthesis in accordance with claim 1, wherein said prosthetic element is composed of metal.

3. A prosthesis in accordance with claim 2 wherein said treatment to eliminate said weak boundary layer comprises degreasing said metal prosthetic element with an alkaline reagent and thereafter treating said prosthetic element with an acidic reagent.

4. A prosthesis in accordance with claim 3, wherein said alkaline reagent comprises an aqueous solution of an alkaline compound and said acidic reagent comprises an aqueous solution of an acidic compound.

5. A prosthesis in accordance with claim 4, wherein said degreasing treatment is carried out at a temperature of from about 200 to 220° F.

6. A prosthesis in accordance with claim 4, wherein said metal prosthetic element consists essentially of a cobalt-chromium-molybdenum alloy.

7. A prosthesis in accordance with claim 6, wherein said alkaline compound comprises sodium hydroxide.

8. A prosthesis in accordance with claim 7, wherein said acid treatment comprises an acid etching treatment followed by a desmutting and passivation treatment.

9. A prosthesis in accordance with claim 8, wherein said acid etching treatment comprises treating said prosthetic element with sulfuric acid and wherein desmutting and passivation treatment comprises treating said prosthetic element with an aqueous admixture of hydrofluoric acid and nitric acid.

10. A prosthesis in accordance with claim 3, wherein said prosthetic element is composed of stainless steel.

11. A prosthesis in accordance with claim 3, wherein said prosthetic element is composed of cobalt-chromium-molybdenum alloy.

12. A prosthesis in accordance with claim 3, wherein said prosthetic element is composed of a titanium alloy.

13. A prosthesis in accordance with claim 1, wherein said prosthetic element is composed of ultra high molecular weight polyethylene.

14. A prosthesis in accordance with claim 13, wherein said treatment to eliminate said weak boundary layer comprises oxidizing said surface.

15. A prosthesis in accordance with claim 14, wherein said surface oxidation treatment comprises acid treatment.

16. A process in accordance with claim 1, wherein said application of said polymethylmethacrylate film to said treated surface comprises providing a solution of polymethylmethacrylate and applying said solution to said treated surface.

17. A prosthesis in accordance with claim 16, wherein the solvent for said polymethylmethacrylate comprises dichloromethane.

18. A prosthesis in accordance with claim 17, wherein said solution additionally comprises barium sulfate.

19. A prosthesis in accordance with claim 16, wherein said annealing treatment comprises heating said prosthetic element bearing said film of polymethylmethacrylate to a temperature of greater than 80° C.

20. A prosthesis in accordance with claim 1, wherein said annealing treatment comprises heating said prosthetic element bearing said polymethylmethacrylate film to a temperature of greater than 80° C.

21. A prosthesis in accordance with claim 20, wherein said prosthetic element is composed of metal.

22. A prosthesis in accordance with claim 20, wherein said prosthetic element is composed of ultra high molecular weight polyethylene.

23. A prosthesis in accordance with claim 1, comprising a bone implant prosthesis.

24. A prosthesis in accordance with claim 1 which has a structure adapted to be fixedly attached to an articular surface of a bone.

25. A prosthesis in accordance with claim 24, wherein said articular surface of said bone comprises the ball portion of a ball and socket joint.

26. A prosthesis in accordance with claim 1, wherein said polymethylmethacrylate layer has a thickness greater than about 0.0001 inch.

27. A prosthesis in accordance with claim 1 wherein said treatment to eliminate any weak boundary layer comprises a mechanical treatment.

28. A prosthesis in accordance with claim 27 wherein said mechanical treatment comprises blasting with alumina grit.

29. In combination, a prosthesis as defined in claim 1 fixedly adhered to a bone by bone cement comprising polymethylmethacrylate.

30. The combination of claim 29 wherein said prosthesis is a bone implant prosthesis.

31. The combination of claim 29 wherein said prosthesis is attached to an articular surface of said bone.

32. A process for preparing an improved prosthesis adapted to be joined to bone by means of bone cement which comprises:
  treating said prosthetic element surface to eliminate any weak boundary layer;
  applying a polymethylmethacrylate film to said treated surface;
  and thereafter annealing said polymethylmethacrylate film.

33. A process in accordance with claim 32, wherein said prosthetic element is composed of metal.

34. A process in accordance with claim 33 wherein said treatment to eliminate said weak boundary layer comprises degreasing said metal prosthetic element with an alkaline reagent and thereafter treating said prosthetic element with an acidic reagent.

35. A process in accordance with claim 34, wherein said alkaline reagent comprises an aqueous solution of an alkaline compound and said acidic reagent comprises an aqueous solution of an acidic compound.

36. A process in accordance with claim 35, wherein said degreasing treatment is carried out at a temperature of from about 200° to 220° F.

37. A process in accordance with claim 35, wherein said metal prosthetic element consists essentially of a cobalt-chromium-molybdenum alloy.

38. A process in accordance with claim 35, wherein said alkaline compound comprises sodium hydroxide.

39. A process in accordance with claim 35, wherein said acid treatment comprises an acid etching treatment followed by a desmutting and passivation treatment.

40. A process in accordance with claim 39, wherein said acid etching treatment comprises treating said prosthetic element with sulfuric acid and wherein desmutting and passivation treatment comprises treating said prosthetic element with an aqueous admixture of hydrofluoric acid and nitric acid.

41. A process in accordance with claim 32, wherein said prosthetic element is composed of ultra high molecular weight polyethylene.

42. A process in accordance with claim 41, wherein said treatment to eliminate said weak boundary layer comprises oxidizing said surface.

43. A process in accordance with claim 42 wherein said surface oxidation treatment comprises acid treatment.

44. A process in accordance with claim 32, wherein said application of said polymethylmethacrylate film to said treated surface comprises providing a solution of polymethylmethacrylate and applying said solution to said treated surface.

45. A process in accordance with claim 44, wherein the solvent for said polymethylmethacrylate comprises dichloromethane.

46. A process in accordance with claim 44, wherein said annealing treatment comprises heating said prosthetic element bearing said film of polymethylmethacrylate to a temperature of greater than 80° C.

47. A process in accordance with claim 32, wherein said annealing treatment comprises heating said prosthetic element bearing said polymethylmethacrylate film to a temperature of greater than 80° C.

48. A process in accordance with claim 32, wherein said prosthesis is a bone implant prosthesis.

49. A process in accordance with claim 32 wherein said prosthesis has a structure adapted to be fixedly attached to an articular surface of a bone.

50. A process in accordance with claim 32, wherein said polymethylmethacrylate layer has a thickness greater than about 0.0001 inch.

51. A process in accordance with claim 32, wherein said treatment to eliminate any weak boundary layer comprises a mechanical treatment.

52. A process in accordance with claim 51, wherein said mechanical treatment comprises blasting with alumina grit.

53. A prosthesis in accordance with claim 14 wherein said surface oxidation treatment comprises flame treatment.

54. A prosthesis in accordance with claim 14 wherein said surface oxidation comprises treatment by corona discharge.

55. A prosthesis in accordance with claim 42 wherein said surface oxidation treatment comprises flame treatment.

56. A prosthesis in accordance with claim 42 wherein said surface oxidation comprises treatment by corona discharge.

* * * * *